United States Patent [19]

Yuan

[11] Patent Number: 5,763,424
[45] Date of Patent: Jun. 9, 1998

[54] COMPOSITION AND METHOD FOR STORING NUCLEOTIDE ANALOGS

[75] Inventor: Lung-Chi J. Yuan, San Mateo, Calif.

[73] Assignee: Gilead Sciences, Inc., Foster City, Calif.

[21] Appl. No.: 622,721

[22] Filed: Mar. 26, 1996

[51] Int. Cl.$^6$ .................................................. A61K 31/675
[52] U.S. Cl. ........................... 514/81; 514/86; 514/784; 514/788
[58] Field of Search ........................... 514/81, 86, 784, 514/788

[56] References Cited

U.S. PATENT DOCUMENTS 5,539,082  7/1996  Nielson et al. .......................... 530/300
5,539,083  7/1996  Cook et al. ............................. 530/333

FOREIGN PATENT DOCUMENTS 2284208  5/1995  United Kingdom .

OTHER PUBLICATIONS

Holy et al., "Synthesis of 9-(2-Phosphonylmethoxyethyl)Adenine and Related Compounds," Collection Czechoslovak Chem. Commun., 52:2801–2809 (1987) Month of publication data is unavailable.

Holy et al., "Synthesis of Isomeric and Enantiomeric O-Phosphonylmethyl Derivatives of 9-(2,3-Dihydroxypropyl)Adenine," Collection Czechoslovak Chem. Commun., 52:2775–2791 (1987) Month of publication data is unavailable.

Chu et al., "Nonenzymatic Sequence-Specific Cleavage of Single-Stranded DNA," Proc. Natl. Acad. Sci. USA, 82, 963–967 (Feb. 1985).

Hasegawa et al., "Physiochemical Stability of Pharmaceutical Phosphate So lutions IV. Prevention of Precipitation in Parenteral Phosphate Solutions," J. Parenteral Sci Technology, 36(5), 210–215 (Sep./Oct. 1982); supplied by applicant. Month of publication data is unavailable. Issue Number information is provided whenever possible following the vol. No. in parentheses.

"Particulate Matter in Injections," U.S. Pharmacopoeia 23:1813–1819 (1995) Month of publication data is unavailable. Issue No. has been included whenever possible.

Berger et al., "Interaction of Metal Ions with Polynucleotides and Related Compounds. XIV. Nuclear Magnetic Resonance Studies of the Binding of Copper (II) to Adenine Nucleotides," Biochem 10(10):1847–1857 (1971) Month of publication data is unavailable. Issue No. has been included whenever possible.

Borchert et al., "Particulate Matter in Parenteral Products: A Review," Journal of Parenteral Science and Technology 40(5):212–241 (Oct. 1986).

Collins et al., "The site of metal ion binding in a nickel derivative of adenosine 5'-monophosphate: an X-ray study," Biochem Biophys Acta 402:1–6 (1975) Month of publication data is unavailable. Issue No. has been included whenever possible.

De Meester et al., "X-Ray evidence for adenine N(1)-metal bonding in a cobalt-9-methyladenine complex," Biochem Biophys Acta 324:301–303 (1973). Month of publication data is unavailable. Issue No. has been included whenever possible.

Gagnon et al., "Structure Cristalline du Nitrate de catena-(micro-Methyl-9 Adenine) Argent(I) Hydrate," Acta Cryst. B33:1448–1454 (1977). Month of publication data is unavailable. Issue No. has been included whenever possible.

Hamlin, William E., "General Guidelines for the Visual Inspection of Parenteral Products in Final Containers and In-Line Inspection of Container Components," Journal of the Parenteral Drug Association 32(2):63–66 (Mar. 1978).

Kistenmacher et al., "Structure of Bis(acetylacetonato)(nitro)(2-aminopyrimidine)cobalt(III)," Inorganic Chemistry 17(2):479–481 (1978). Month of publication data is unavailable. Issue No. has been included whenever possible.

Kong et al., "Binding Sites between Platinum (II) and Purine or Pyrimidine Ribosides," Inorganic Chemistry 13(8):1981–1985 (1974) Month of publication data is unavailable.

Lock et al., "Molecular Structure of micro-(9-Methyladenine-N1,N7)-bis(diisopropyl sulfoxide-S)-trans-dichloroplatinum(II)1," J Am Chem Soc 98(24):7865–7866 (Nov. 24, 1976).

Massoud et al., "Metal Ion Coordinating Properties of Pyrimidine-Nucleoside 5'-Monophosphates (CMP, UMP, TMP) and of Simple Phosphate Monoesters, Including D-Ribose 5'-Monophosphate. Establishment of Relations between Complex Stability and Phosphate Basicity," Inorganic Chemistry 27:1447–1453 (1988) Month of publication data is unavailable.

Scheller et al., "Macrochelate Formation in Monomeric Metal Ion Complexes of Nucleoside 5'-Triphosphates and the Promotion of Stacking by Metal Ions. Comparison of the Self-Association of Purine and Pyrimidine 5'-Triphosphates Using Proton Nuclear Magnetic Resonance," J Am Chem Soc 103(2):247–260 (Jan. 28, 1981).

Sigel et al., "Metal-Ion-Coordinating Properties of Various Phosphonate Derivatives, Including 9-[2-(Phosphonylmethoxy)ethyl]adenine (PMEA)—an Adenosine Monophosphate (AMP) Analogue) with Antiviral Properties," Helvetica Chimica Acta 75:2634–2656 (1992), Oct. 17.

(List continued on next page.)

Primary Examiner—John Kight
Assistant Examiner—L. Eric Crane
Attorney, Agent, or Firm—Daryl D. Muenchau

[57] ABSTRACT

The invention provides compositions and methods to prevent the appearance of visually detectable precipitate in the composition upon storage of an aqueous solution of the composition containing 5–250 mg/mL of the phosphonate nucleotide analog for at least 6 months at 22° where the composition comprises a phosphonate nucleotide analog and a sufficient amount of a divalent or trivalent metal cation sequestering agent such as about 0.1% w/v EDTA, and/or a sufficiently low concentration of a divalent or trivalent metal cation, e.g., about 3–10 ppm, and/or a sufficient pH in water, e.g., a pH of about 7.0–7.5.

71 Claims, No Drawings

OTHER PUBLICATIONS

Sternglanz et al., "Interactions of Hydrated Metal Ions with Nucleotides: the Crystal Structure of Barium Adenosine 5'-Monophosphate Heptahydrate," Biochem 15(22):4797–4803 (1976) Month of publication data is unavailable.

Tribolet et al., "Self–association and protonation of adenosine 5'-monophosphate in comparison with its 2'-and 3'-analogues and tubercidin 5'-monophosphate (7–deaza–AMP)," J Biochem 163:353–363 (1987) Month of publication data is unavailable.

COMPOSITION AND METHOD FOR STORING NUCLEOTIDE ANALOGS

BACKGROUND OF THE INVENTION

The present invention relates to methods and compositions for the stable storage of nucleotide analogs.

Sigal et al. (*Helv. Chim. Acta*, (1992) 75:2634–2656) relate to a study of the interaction between nucleotide analogs and cations.

OBJECTS OF THE INVENTION

An object of the invention is to provide compositions and methods to reduce the rate of formation of complexes between phosphonate nucleotide analogs ("PNAs") and divalent or trivalent metal cations that occur on storage.

An object of the invention is to provide compositions and methods to reduce or eliminate the extent of precipitation and/or the size of precipitates, especially visually detectable precipitation, of PNAs that occurs during storage of aqueous solutions containing the PNA and one or more divalent or trivalent metal cations.

An object of the invention is to provide compositions and methods to increase the storage life of aqueous PNA solutions for human or veterinary therapeutic uses or for in vitro diagnostic or research applications.

SUMMARY OF THE INVENTION

Objects of the invention are accomplished by compositions comprising a PNA and (a) a sufficient amount of a sequestering agent, and/or (b) a sufficiently low concentration of a divalent or trivalent metal cation, and/or (c) a sufficient pH in water, to prevent the appearance of visually detectable precipitate in the composition upon storage of an aqueous solution of the composition containing 5–250 mg/mL of the PNA for at least 6 months at 22°. Typically the composition is an aqueous solution, but embodiments include solid compositions that give rise to the aqueous solutions. These embodiments include aqueous PNA solutions containing about 2–250 ppm, often about 4–250 ppm, more often about 5–250 ppm or usually about 8–250 ppm of divalent or trivalent metal cations, and the solid compositions used to prepare these aqueous solutions. Such cation-containing aqueous solutions, and the corresponding solid compositions used to prepare the solutions, will optionally contain about 0.001–0.6% w/v, or more often about 0.01%–0.5% w/v, of a sequestering agent.

Invention embodiments include a composition comprising a sufficiently low concentration of a divalent or trivalent metal cation to prevent the appearance of visually detectable precipitate in the composition upon storage of an aqueous solution of the composition containing 5–250 mg/mL of the PNA for at least 6 months at 22°. Typical divalent or trivalent metal cation concentrations in PNA solutions comprising a sufficiently low metal cation concentration are about 2–20 ppm or more often about 3–18 ppm, usually about 4–15 ppm.

Invention embodiments include a composition comprising a PNA and a sequestering agent. Such aqueous PNA solutions, and the corresponding solid compositions used to prepare the solutions, will optionally contain about 0.001–0.6% w/v, or more often about 0.01%–0.5% w/v, usually about 0.02%–0.4% w/v of a sequestering agent.

Invention embodiments include a product produced by the process of mixing a PNA with a (a) a sufficient amount of a sequestering agent, and/or (b) a sufficiently low concentration of a divalent or trivalent metal cation, to prevent the appearance of visually detectable precipitate in the composition upon storage of an aqueous solution of the composition containing 5–250 mg/mL of the PNA for at least 6 months at 22°.

Objects of the invention are accomplished by a method of storing for a period in excess of about 6 months a composition comprising a PNA and (a) a sufficient amount of a sequestering agent, and/or (b) a sufficiently low concentration of a divalent or trivalent metal cation, and/or (c) a sufficient pH in water, to prevent the appearance of visually detectable precipitate in the composition upon storage of an aqueous solution of the composition containing 5–250 mg/mL of the PNA for at least 6 months at 22°.

DETAILED DESCRIPTION OF THE INVENTION

Unless otherwise indicated, temperatures are in degrees Celsius (°). The unit ppm means jig of metal cation per g of PNA, unless otherwise specified.

As used herein, alkyl means saturated hydrocarbon moieties, including linear, branched and cyclic forms. Exemplary alkyl include alkyl groups having 1, 2, 3, 4, 5, 6, 7, 8, 9, 10, 11, 12, 13, 14, 15, 16, 17, 18, 19, 20 or more carbon atoms, unless the disclosure or context specifies otherwise. Alkyl groups can comprise methyl, ethyl, propyl, isopropyl, butyl, sec-butyl, t-butyl, pentyl, isopentyl, neopentyl, n-hexyl, 1-methylpentyl, 2-methylpentyl, 1-ethylbutyl, 2-ethylbutyl, 3-ethylbutyl, cyclohexyl, n-heptyl, 2-ethylpentyl, n-octyl, cyclooctyl, 1-ethylhexyl, 2-ethylhexyl, 3-ethylhexyl, n-nonyl, and n-decyl.

As used herein, divalent or trivalent metal cations include $Fe^{3+}$, $Fe^{2+}$, $Ca^{2+}$, $Ba^{2+}$, $Ni^{2+}$, $Mg^{2+}$, $Cu^{2+}$, $Mn^{2+}$, $Co^{2+}$, $Sr^{2+}$, $Cr^{3+}$, $Al^{3+}$, $La^{3+}$, $Tb^{3+}$, $Cd^{2+}$ and/or $Zn^{2+}$.

Sequestering Agent. As used herein, sequestering agent means an agent or compound that can bind to or complex with divalent or trivalent metal cations whereby a solution containing a PNA and one or more the ions does not form visually detectable precipitate when the solution is stored for an extended time, e.g., 6 months at 22°. Exemplary sequestering agents include chelating agents and cation exchange resins. Suitable cation resins include commercially available resins such as Chelex™, Diaion™, Duolite™, agarose-linked tris(2-aminoethyl)amine and agarose-linked tris (carboxymethyl)ethylenediamine (Sigma, St. Louis, Mo.). Chelating agents include nitrilotriacetic acid, aminopolycarboxylic acids, e.g., EDTA (ethylenediaminetetraacetic acid), EGTA (ethylene-bis-oxyethylenenitroltetraacetic acid) and their salts, hydroxycarboxylic acids, e.g., citric, gluconic and tartaric acids and their salts and crown ethers. The sequestering agent does not need to be water soluble, but ordinarily it is soluble in therapeutic PNA compositions. If the sequestering agent is not water soluble then it is advantageously disposed in the container for the PNA. It usually is in the form of an article such as a membrane, wool, beads, liner or other formed shape that is readily separable from the PNA composition, whereby it rests in the PNA composition or solution and adsorbs cations in situ.

Phosphonate Nucleotide Analogs. PNAs are generally known and available to the artisan by generally known methods. PNAs are generally are of the formula $(HO)_2P(O)$—R—B wherein B is a purine base or a pyrimidine base, generally B is a purine base, usually adenin-9-yl, guanin-9-yl, 2,6-diaminopurin-9-yl, 6-aminopurin-9-yl or a protected analog of any of these bases;

R is —CHR⁷—R¹¹—(CH₂)ₘ₁—C(R⁸)((CH₂)ₘ₂(R⁹))—((CH₂)ₘ₃—R¹⁰—(CH₂)ₘ₄—, —Q—C₆H₄—CH₂—, CHR⁷—O—CHR⁷—O—CHR⁷—, —CHR⁷—(CHR¹³)ₘ₁—CHR¹⁴—R¹⁰—,

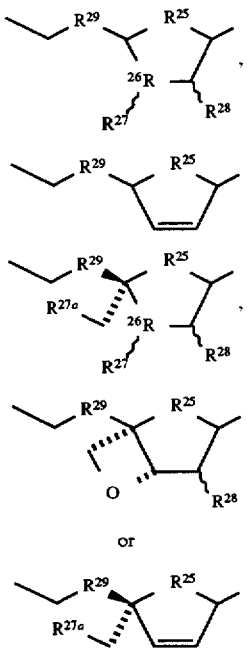

but ordinarily R is —CH₂O(CH₂)₂—, —CH₂OCH(CH₂OH)CH₂—, —CH₂OCH(CH₃)CH₂— or a compound of structure II where R²⁵ and R²⁹ are both oxygen;

R⁷ is H or C₁-C₄ alkyl, but typically H;

R⁸ is H or C₁-C₄ alkyl, C₂-C₄ alkenyl, azidomethyl or azidoethyl, but usually H, vinyl or azidomethyl;

R⁹ is halogen (F, Cl, Br or I), H or OH, usually H or OH;

R¹⁰ is O, CH₂ or a chemical bond, but typically O;

R¹¹ is O, S, CH₂, CHF or CF₂;

Q is —C(R^{f2})2—CH₂—, —C(R¹²)₂—O—, —CR¹²=CR¹²—, or —C≡C—, wherein each R^{f2} is independently H, or halogen;

R¹³ is H, halogen, OH, CH₃, CH₂OH, or C₃-C₆ acyloxymethyl;

R¹⁴ is H, halogen, OH, CH₃, CH₂OH, C₃-C₆ acyloxymethyl, or C₂-C₆ acyloxy;

R²⁵ is CH₂, CHF or O, usually O;

R²⁶ is CH or S;

R²⁷ is H, OH, halogen, N₃, C₁-C₄ alkyl, C₁-C₄ alkoxy or, when R²⁶ is S, R²⁷ is absent;

R²⁷a is H, OH, halogen, N₃, C₁-C₄ alkyl, C₁-C₄ alkoxy;

R²⁸ is H, OH, halogen, N₃, C₁-C₄ alkyl or C₁-C₄ alkoxy;

R²⁹ is O, S, CH₂, CHF, CF₂, typically O, n2 is an integer having a value from 0 to 6;

m1 is an integer having a value from 0 to 4, usually 0;

m2 is an integer having a value from 0 to 4, usually 0 or 1;

m3 is an integer having a value from 0 to 4, usually 0 or 1;

m4 is an integer having a value from 0 to 4, usually 0 or 1; and wherein substituents linked to chiral carbon atoms are in the R, S or RS configuration, unless otherwise specified. In the R structures shown above, B is attached to the open bond at the right side of the structure and the phosphorus atom is linked to the open bond on the left side.

PNAs typically include compounds such as 9-[2-(phosphonomethoxy)ethyl]adenine (PMEA), 9-[2-(phosphonomethoxy)propyl] adenine (PMPA), 9-[2-(phosphonomethoxy)propyl] 2,6-diaminopurine (PMPDAP), [2,5-dihydro-5-(phosphonomethoxy)-2-furanyl] adenine (D4AP) and 9-[2-(phosphonomethoxy)ethyl] guanine (PMEG). Protecting groups for the exocyclic amine or hydroxyl groups which are groups present in purine and pyrimidine bases have been described (T. W. Greene et al., eds., *Protective Groups in Organic Synthesis* (1991), Wiley, 2nd ed.).

An adenyl-containing PNA is a PNA having an adenine base or a protected adenine base. Exemplary protected adenine bases include adenine having the exocyclic amine group protected with —C(O)R¹ where R¹ is phenyl or C₁₋₁₀ alkyl, usually methyl, ethyl or propyl. Protected adenine bases also include protected derivatives where the exocyclic amine group is protected with =CR²—N(R³)₂ where R² is H or CH₃ and each R₃ is independently C₁₋₈ alkyl, usually methyl, butyl or isobutyl. Exemplary adenyl-containing PNAs include adenine-protected PMEA and adenine-protected PMPA. Adenyl-containing PNAs usually comprise unprotected adenine.

Some of these compounds are in clinical development. For example, PMEA cyclic HPMPC, HPMPC, PMPA and other PNAs have been considered for, or are, in development as parenteral products for the treatment of viral infections. In the course of preparing PMEA intravenous injection formulations, I discovered that the preparations formed visibly detectable particulate matter or precipitates under extended storage at ambient temperature. Similar particulates were discovered in stored PMPA formulations as well. The visible particles that formed in PMEA solutions were analyzed by energy-dispersive x-ray spectrometry (EDX) and Fourier transform infrared spectroscopy and were determined to be metal ion-PMEA complexes. The principal metal ions associated with the particulates were iron (Fe³⁺) and zinc (Zn²⁺), which were present at <40 ppm, i.e., <0.004% by weight of PMEA, in aqueous solutions of commercial PMEA bulk drug, as determined by inductively coupled argon plasma emission spectroscopy (ICAPES). Having identified a problem heretofore unappreciated, I realized that ameliorating it could be accomplished by a number of routes or their equivalents, as will be discussed below.

Method to Visually Detect Precipitate in an Aqueous PNA Solution. One visually detects precipitate by employing one who is capable, in at least 70% of cases where such precipitate exists, of visually observing in clear aqueous solutions at least 1 particle/mL where the particle is opaque and has a maximum effective linear dimension of at least 50 μm. Visual observation conditions for parenteral solutions have been previously described (M. J. Akers, *Parenteral Quality Control: Sterility, Pyrogen, Particulate and Package Integrity Testing*, 2nd edition, 1994, Marcel Dekker, Inc., New York, N.Y., Chapter 3, p. 175–245, see p. 185–194; Hamlin, *J. Parenteral Drug Assoc.*, (1978) 32:63).

Methods of Reducing Precipitate Formation. Several methods are suitable to prevent visually detectable precipitation of PNAs from aqueous solutions containing divalent and/or trivalent metal cation.

They generally fall into three classes. First, one can modify the PNA manufacturing method, reagents and bulk compound storage containers as needed to avoid the introduction of divalent or trivalent metal cations. Exemplary steps are to use glass lined reactors and piping, test starting materials and reagents for metal ions and remove contaminant metal if required or shift to an alternative supplier, and other techniques that will be apparent to the ordinary artisan.

Secondly, one can remove the metal ions from intermediates or, preferably, final product, during or at the termination of bulk compound manufacture. "Removal" means both physically extracting sufficient of the ions from the compositions containing the PNA as well as removing the ions from the molecular, i.e., complex-forming, interaction with the PNA by the intercession of an exogenous binding or sequestering agent. Extraction optionally is done during PNA manufacture by selecting intermediate purification procedures to separate out metal ions, e.g., by introducing a counterion to precipitate the metal ion, using a resin to adsorb the ion and then recovering the PNA free of the resin, and other methods that will be immediately apparent to the artisan.

The ions can be removed during storage of the final product or at the completion of bulk compound manufacture. This involves adsorbing or binding the ions in or into a discrete phase, e.g., a solid or oil, that is separate from the PNA, but more typically comprises binding the ions to a water soluble substance for which the ions have a greater affinity than the PNA in the composition concerned and under the conditions of storage expected. For example, a sequestering agent is added to the product, either as a soluble compound such as a chelating agent, or as an adsorptive phase-discrete article or lining in the storage container for the PNA as discussed further above.

Third, one can adjust the conditions of storage so as to create conditions that are unfavorable for the formation of cation-PNA precipitates. A typical option is the use of low temperature or of suitable pH adjustments as will be more fully described below. The latter is preferred over low temperature storage for economic reasons.

Other methods for achieving equivalent goals will be apparent to the artisan and shall be considered to be within the scope of this invention.

It will be understood that one or more of the foregoing alternatives are suitably used. For example, pH adjustments can be combined with a chelating agent. Glass-lined reactors and piping can be used together with an anion exchange resin cap liner in the product vial. In addition, the artisan will appreciate that use of more than one alternative will lessen the degree with which each alternative is employed. For example, if the initial ion concentration has been reduced by manufacturing measures, or the composition is stored at more basic conditions, the concentration of sequestering agent can be reduced or may be eliminated. The possible combination steps are manifold and well within the ordinary skill of the artisan to determine. All that is needed is to prepare sample PNA compositions, store them for the requisite period, and evaluate them for the appearance of visual precipitates. Suitable matrix experiments will be readily apparent and would not require undue experimentation.

Removal of Metal Cations From Contact with PNA. When a sufficient amount of a sequestering agent is present in an aqueous PNA solution, the sequestering agent effectively eliminates precipitate formation by reducing the amount of free ion available for complexing with the PNA. One can optionally determine the concentration of a given sequestering agent that is needed to prevent formation of visually detectable precipitate for 6 months at 22° by using a PNA solution containing a given amount of one or more divalent or trivalent metal cations. For example, one would prepare a solution that contains known amounts of the PNA, ion(s) and other solution components such as buffer. One would then prepare aliquots of this solution containing differing amounts of a selected sequestering agent, e.g., 0.001–0.6% of a chelating agent such as EDTA using about 10–20 different EDTA concentrations with a control containing no EDTA, and store the aliquots in a sealed clear glass container or vial for 6 months at 22°. At the end of 6 months of storage, one would visually examine the vials to determine the minimal concentration needed to prevent formation of visually detectable precipitate. One could optionally repeat this process one or two times to further define the concentration of sequestering agent that is needed to prevent formation of visually detectable precipitation under the selected storage conditions. In performing this assay, one could optionally use 2–6 or more vials, with each having the same solution and sequestering agent concentration to insure that a result at each tested sequestering agent concentration was reproducible. One optionally performs the assay using solutions containing any PNA concentration and/or additive, e.g., buffer, of interest. In general, one would need to use less, or omit, the sequestering agent when the ion concentration is sufficiently low, e.g., about 3–15 ppm or about 4–12 ppm, or when the ion's binding affinity with the PNA is low relative to its binding affinity with the sequestering agent.

An exemplary embodiment comprises a solution at a pH of about 6.0–7.5 containing about 25–100 mg/mL of a PNA, about 0.1 mg/mL of disodium EDTA or about 25 mg/mL of citric acid as the chelating agent and about 10–60 ppm of divalent or trivalent metal cation. Another exemplary embodiment comprises a solution at a pH of about 6.0–7.5 (or at about 4.0–5.0), containing about 25 mg/mL of PMPA, about 0.1 mg/mL of disodium EDTA as the chelating agent and about 10–60 ppm of divalent or trivalent metal cation. Another exemplary embodiment comprises a solution at a pH of about 7.0–7.5 containing about 75 mg/mL of PMEA, about 0.1 mg/mL of disodium EDTA as the chelating agent and about 10–60 ppm of divalent or trivalent metal cation. In any of these embodiments, the predominant metal cation is optionally $Fe^{3+}$ or is optionally $Zn^{2+}$.

Adjustment of Conditions of Storage. Another method to optionally prevent the formation of visually detectable precipitate from the aforementioned aqueous PNA solutions is to adjust the solution pH to prevent precipitation when one stores the solution for 6 months at 22°. In general the pH of a PNA solution will be about 3.5–9.0, often about 4.5–8.0, usually about 7.0–7.5. Here, one would determine the optimum pH for stability by preparing a solution that contains known amounts of the PNA, ion(s) and other solution components such as an ion sequestering agent and/or buffer. One would then prepare aliquots of this solution having differing pH values, e.g., using a pH range of 3.5–9.0 with about 10–20 different tested pH values, and store the aliquots in a sealed clear glass container or vial for 6 months at 22°. At the end of 6 months of storage, one would visually examine the vials to determine the pH values where formation of visually detectable precipitate did not occur. One optionally repeats this process one or two times to further define the pH that is needed to prevent formation of visually detectable precipitation under the selected storage conditions. In performing this assay, one could optionally use 2–6 or more vials at a given pH, with each vial having the same solution and ion concentration to insure that a result at each tested pH was reproducible. One optionally performs the assay using solutions containing any PNA concentration and/or additive, e.g., buffer, of interest. In general, one would use sufficiently low ion concentrations, e.g., about 3–15 ppm or about 4–12 ppm, particularly where the contaminating ions have a relatively low binding affinity with the PNA, e.g., $Mg^{2+}$.

Establishing Low Total Concentrations of Metal Ion. One may also optionally prevent the formation of visually detectable precipitate from an aqueous PNA solution by insuring a sufficiently low divalent or trivalent metal cation concentration. In general, a divalent or trivalent metal cation concentration of about 2–15 ppm or about 4–12 ppm and usually about 5–8 ppm is sufficiently low. These low levels of metal cation typically represent a mole ratio of metal cation to PNA of about $0.8–1.4 \times 10^{-5}$, depending on the PNA and metal ion(s) that are present. For example, optimally low concentrations of metal ion are determined by preparing a solution containing known amounts of the PNA and other solution components such as buffer together with differing amounts of one or more divalent or trivalent metal cations, e.g., total cation of about 4–12 ppm using about 10–20 different cation concentrations with a control containing no cation. The aliquots are then stored in a sealed clear glass container or vial for 6 months at 22°. At the end of 6 months of storage, one would visually examine the vials to determine the minimal concentration needed to prevent formation of visually detectable precipitate. One could optionally repeat this process one or two times to further define a sufficiently low cation concentration that is needed to prevent formation of visually detectable precipitation under the selected storage conditions. In performing this assay, one could optionally use 2–6 or more vials, with each having the same solution and cation concentration to insure that a result at each tested cation concentration was reproducible. One optionally performs the assay using solutions containing various PNA concentrations and/or additives, e.g., a buffer. In general, one could have more cation, e.g., about 8–12 ppm, when the pH is sufficient, e.g., about 7.5–8.0 for $Fe^{3+}$, to reduce the rate or amount of precipitate that is formed under the storage conditions, or when a sequestering agent is present.

As noted above, one may also optionally use a combination of two or three of (1) having a sequestering agent present in the solution, and/or (2) a sufficient pH and/or (3) a sufficiently low level of divalent or trivalent metal cation to reduce or eliminate formation of visually detectable precipitate. To determine conditions sufficient to prevent the formation of visually detectable precipitate under defined storage conditions, one would perform the test in a manner similar to that described above using selected storage conditions and an aqueous PNA solution having selected components present. Usually, the aqueous invention PNA solutions will contain at most about 150 ppm, usually about 100 ppm and at least 2, 3, 4, 5 ppm or more of divalent or trivalent metal cation and typically the solutions will contain about 4–150 ppm, often about 5–100 ppm, usually about 10–60 ppm of such metal cations.

All cited references are incorporated herein by reference.

EXAMPLES

The following examples illustrate but do not limit the invention.

Example 1

Recovery of PMEA-Metal Cation Complexes. Four different preparations of PMEA drug substance (preparations A, B, C, D) were utilized in the preparation of four different lots of PMEA intravenous (I.V.) injection (preparation numbers 1, 2, 3 and 4) which were analyzed as discussed in the Examples below.

PMEA I.V. injection was prepared as a single use vial formulated at pH 6.5 with a concentration of 75 mg/mL of PMEA in water. The pH was adjusted with NaOH or HCl as needed. The solution was held at 30° and then monitored for appearance, potency, pH, sterility, and particulate matter. Visual examination of the PMEA drug product in a standard black background white light box revealed varying degrees of particulate formation. Other attributes of the product quality such as potency, pH, and sterility were unaffected.

We collected the particulates from 25 mL of the PMEA I.V. injection (preparation 4) containing 35 ppm of iron content by centrifuging the PMEA solutions at 15,000 rcf for 15 min. The particulates were washed once with 5 mL water to remove un-complexed drug. This collected sample was dried under vacuum overnight and provided the source of particulates for further spectroscopic analysis. This sample is referred to as "Isolated Sample" herein.

Example 2

Preparation of PMEA-Fe Complex. Authentic PMEA-Fe complex was prepared by adding about 250 ppm of ferric ion ($Fe^{3+}$) into PMEA solution (75 mg/mL at pH 6.5). This PMEA preparation was stored at 70° C. for two days. We recovered the particulates as described in Example 1. This sample is referred as "Authentic Sample" herein.

Ferric chloride hexahydrate was analytical grade and purchased from Mallinckrodt Specialty Chemicals Co. (Paris, Ky.). Zinc sulfate monohydrate was analytical grade and purchased from Aldrich Chemical Company, Inc. (Milwaukee, Wis.). Ethylenediaminetetraacetic acid, disodium salt dihydrate (EDTA) and citric acid were U.S.P./N.F. grade and purchased from Spectrum Chemical Mfg. Corp. (Gardena, Calif.).

Example 3

Temperature and Ion Concentration Dependence Study. PMEA preparations (75 mg/mL at pH 6.5) containing about 24 ppm of iron were stored at 40°, 50°, 60°, and 70° C. The iron concentration (ppm) was calculated relative to the amount of PMEA in solution. The rate of particulate formation was followed by visual examination of each vial against a black/white background light box until 50% of studied vials showed visible particulates. Particulate matter formation in PMEA I.V. injection was temperature dependent as shown below, with the appearance of visible particulates occurring sooner at higher temperatures.

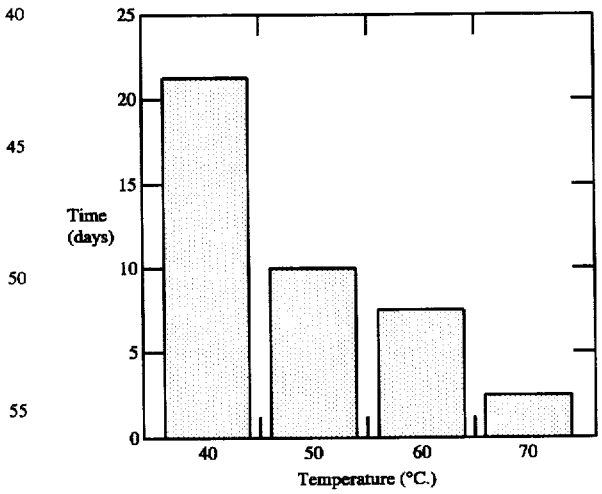

The temperature dependency for particulate matter formation in PMEA solutions was non-linear. At 50°–70° C., the rate of particulate formation for the PMEA solutions containing 24 ppm of iron was less than 10 days. When the temperature was lower than 50° C., the rate of particulate formation decreased abruptly. At 40° C., particulate matter formation was observed after 22 days. At a storage temperature of 30° C., particulate matter formation was observed after a few months. Under refrigeration (4° C.), particulate matter formation was not observed even after 18 months.

The degree of particulate matter formation in PMEA solutions increased with time.

The rate of particulate matter formation in PMEA solutions was dependent on the concentration of metal ions. Four concentrations (17, 40, 75, 132, and 246 ppm) of $Fe^{3+}$ ion were added to PMEA solutions (75 mg/mL at pH 6.5) and stored at 70° C. A visual examination was carried out to determine the rate of particulate formation. The data shown below demonstrated that the increase of the concentration of $Fe^{3+}$ ion resulted in reducing the time needed to generate visually detectable particulates in PMEA solutions. The time required for appearance of precipitate is shown below. Similar data was obtained for $Zn^{2+}$ ion with PMEA solutions.

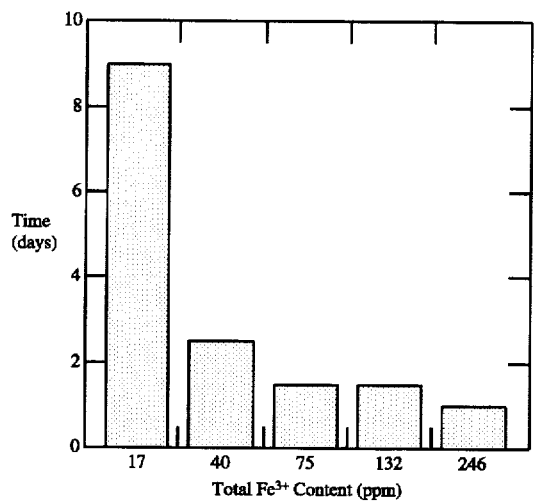

Example 4

Characterization of Particulate Matter. EDX equipped with an electron microscope has been used for characterizing particulate matter in injectables (see e.g., Borchert et al., *J. Parenteral Sci.*, (1986) 40:212–241). EDX provides elemental information by measuring the energy of the x-ray emitted from the sample, when the material is exposed to an electron beam. This technique is semi-quantitative with a relative accuracy of 10–25%, but it provides information regarding the composition of particulate matter.

Table I summarizes the EDX results of particulate matter present in the four PMEA I.V. injection preparations described in Example 1 and the particulates in the Isolated and Authentic Samples.

TABLE I

| | Analyses Particles Using EDX Spectrometry | | | | | | |
|---|---|---|---|---|---|---|---|
| | PMEA (%) | Particles in 1 (%) | Particles in 2 (%) | Particles in 3 (%) | Particles in 4 (%) | Isolated Sample (%) | Authentic Sample (%) |
| C | 46 | 47 | 39 | 38 | 35 | 37 | 40 |
| N | 26 | 19 | 23 | 28 | 29 | 27 | 24 |
| O | 21 | 22 | 26 | 26 | 25 | 25 | 25 |
| P | 6.5 | 3.9 | 3.3 | 3.9 | 4.9 | 4.2 | 4.9 |
| Zn | — | 8.5 | 8.1 | — | — | — | — |
| Fe | — | — | — | 4.3 | 6.0 | 6.0 | 5.2 |

The data indicated that in addition to the expected carbon, nitrogen, oxygen, and phosphorous associated with the parent compound (PMEA), the predominant metal ions associated with the particulates were iron and zinc. Particulate residues from preparation numbers 1 and 2 contained a large zinc content, and particulate residues from preparation numbers 3 and 4 contained a large iron content. Data in Table I suggested that particulates in preparations 1 and 2 were PMEA-Zn complexes, and particulates in preparations 3 and 4 were PMEA-Fe complexes. Based on EDX results, the molar ratio between iron and PMEA appeared to be 1:2.5.

Example 5

Identification of Metal Contents. We analyzed iron and zinc concentrations in the PMEA drug product solutions and the corresponding PMEA drug substances preparations by ICAPES. The data is shown in Table II.

TABLE II

| Analysis of Iron and Zinc by ICAPES. | | | |
|---|---|---|---|
| I.V. Drug Product Preparation | Fe/Zn (ppm) | Corresponding Drug Substance[b] | Fe[a] (ppm) |
| 1 | 1.9/4.3 | A | 2.8 |
| 2 | 7.7/3.1 | B | 12 |
| 3 | 17/1.2 | C | 28 |
| 4 | 24/1.3 | D | 35 |

[a]The level of zinc content in PMEA drug substance was not determined.
[b]Solid PMEA preparation used for each corresponding I.V. preparation (see Example 1).

In this technique, an atomic spectrum is excited in inductively coupled argon plasmas and it is used for simultaneous trace multielement analyses. This analysis was used to determine the impact, if any, of the drug product manufacturing process and the container/closure system used in the finished product. Also, the ICAPES data verified the semi-quantitative EDX data with regard to the predominant metal species associated with the particulates found in each lot of bulk PMEA drug product.

Inspection of data in Table II demonstrated that the levels of iron in PMEA finished product and the corresponding drug substance were consistent. Therefore, the metal ions contributing to the insoluble complex formation were present in the PMEA drug substance. Furthermore, preparations 1 and 2 were comparable in terms of their levels of zinc metal, which had been previously identified as a major component in the particulates by EDX analysis, whereas preparations 3 and 4 were both characterized by relatively high levels of iron in comparison with other metal species present. This result was consistent with the conclusion that the particulates were the result of insoluble drug-metal complexes. Data summarized in Table II also revealed that the levels of iron and zinc present were relatively low (1–35 ppm) indicating a high affinity between PMEA and iron or zinc.

Example 6

Effect of pH on the Rate of Particulate Formation. Particulate matter formation in PMEA solutions was also found to be affected by pH. PMEA solutions prepared at pH 6.5 with an iron ($Fe^{3+}$) content of about 2 ppm did not form visible particulates after 2 months of storage at 70° C. However, in a similar preparation, but with a final pH adjustment at pH 5.8, particulate matter was observed after 3 weeks of storage at 70° C. Another study was carried out using PMEA solutions with a higher iron content (58 ppm) at pH 6.5 and 7.4. PMEA solutions prepared at pH 6.5 showed visible particles after 3 days of storage at 70° C., but PMEA solutions prepared at pH 7.4 showed no visible particles even after 4 weeks of storage at 70° C. Data showed that PMEA solutions prepared at higher pH delayed particulate matter formation significantly.

Example 7

Effect of Chelating Agents on Particulate Formation. Addition of EDTA (0.01% w/v) or citrate (25 mM) successfully prevented particulate matter formation in PMEA solutions. Table III summarizes the particulate counts of a PMEA solution (75 mg/mL, pH 6.5) in the presence of 75 ppm of iron and 0.01% EDTA stored at 4°, 30°, and 70° C., for periods of 1, 2 and 5 months. Particulate counts were obtained essentially as described in the U.S.P. membrane filtration method for large volume injections (U.S. Pharmacopoeia, vol. 23, 1995, method 788, *Particulate Matter in Injections*, p. 1813–1819, U.S. Pharmacopeial Convention, Inc, Rockville, Md.). The particulate counts shown in Table III are the total particles that were present in each tested 5.0 mL sample.

TABLE III

Particulate Counts of a PMEA Solution[1] Using the USP Membrane Filtration Method.

|  | 4° C. | | 30° C. | | 70° C. | |
| --- | --- | --- | --- | --- | --- | --- |
|  | ≥10 μm | ≥25 μm | ≥10 μm | ≥25 μm | ≥10 μm | ≥25 μm |
| Initial[2] | 314 | 24 | 314 | 24 | 314 | 24 |
| 1 | — | — | — | — | 518 | 47 |
| 2 | — | — | 501 | 72 | 782 | 103 |
| 5 | 551 | 61 | 681 | 82 | 1076 | 275 |

[1]PMEA solutions used in this study had a volume of 5.0 mL and contained 75 mg/mL of PMEA at pH 6.5 in the presence of 75 ppm of iron and 0.01% EDTA.
[2]Initial indicates particulates observed in freshly prepared solutions and the numbers below initial represent the time in months that the solution was stored prior to assay for particulates.

As shown in Example 3 above, visible particles would be expected to form after two days of storage at 70° C. in a PMEA solution containing 75 ppm of iron. Nevertheless, addition of 0.01% EDTA significantly inhibited the observation of visible particles.

Particulates observed in PMEA solutions could be re-dissolved by spiking the solution with 0.02% w/v EDTA and with a pH adjustment of 7.4. Following the storage at 70° C. for one week, visible particulate matter gradually disappeared.

Example 8

Particulate Formation in PMPA Solutions. Tables 1–4 summarize visual observations of particulates in PMPA solutions that were stored at 4° C. or 60° C. All formulations were prepared using a PMPA concentration of 75 mg/mL and the pH was adjusted to pH 6.5 or 7.5 using NaOH or HCl as needed. Soluble iron and zinc were added as $FeCl_3$ and $ZnCl_2$. Metals were added at solution concentrations which reflect drug substance concentrations of 50 and 100 ppm. Thus, in a PMPA solution concentration of 75 mg/mL, a metal concentration of 50 and 100 ppm in the PMPA corresponds to a solution concentration of 3.75 ppm and 7.5 ppm respectively.

Precipitation was greater at 60° C. than at 4° C. (Tables 1 vs. 3 and Tables 2 vs. 4). At both storage conditions, precipitation appeared more prevalent at pH 6.5 than at pH 7.5 (Tables 1 vs. 2 and Tables 3 vs. 4). Zinc metal ions enhanced precipitation to a greater extent than $Fe^{3+}$ (Tables 1–4). The presence of EDTA, disodium dihydrate (0.01% w/v), inhibited precipitation under all conditions tested (Tables 1–4).

We evaluated the effect of EDTA concentration on inhibition of precipitation at pH 6.5, 100 ppm $Zn^{2+}$ and storage at 4° C. and 60° C. (Tables 5 and 6). As the concentration of EDTA was reduced below 0.01% w/v, the presence of visibile precipitation increased. Precipitation was greater at the higher storage temperature.

TABLE 1

Samples at 75 mg/mL PMPA, pH 6.5, 4° C. Storage

| Time (days) | 50 ppm $Fe^{3+}$ no EDTA | 50 ppm $Fe^{3+}$ + EDTA | 100 ppm $Fe^{3+}$ no EDTA | 100 ppm $Fe^{3+}$ + EDTA | 50 ppm $Zn^{2+}$ no EDTA | 50 ppm $Zn^{2+}$ + EDTA | 100 ppm $Zn^{2+}$ no EDTA | 100 ppm $Zn^{2+}$ + EDTA |
| --- | --- | --- | --- | --- | --- | --- | --- | --- |
| 9 | − | − | − | − | + | − | ++ | − |
| 16 | − | − | − | − | ++ | − | ++ | − |
| 24 | − | − | − | − | + | − | + | − |
| 46 | − | − | − | − | + | − | ++ | − |

+ = precipitate observed
++ = heavy precipitate observed

TABLE 2

Samples at 75 mg/mL PMPA, pH 7.5, 4° C. Storage

| Time (days) | 50 ppm $Fe^{3+}$ no EDTA | 50 ppm $Fe^{3+}$ + EDTA | 100 ppm $Fe^{3+}$ no EDTA | 100 ppm $Fe^{3+}$ + EDTA | 50 ppm $Zn^{2+}$ no EDTA | 50 ppm $Zn^{2+}$ + EDTA | 100 ppm $Zn^{2+}$ no EDTA | 100 ppm $Zn^{2+}$ + EDTA |
| --- | --- | --- | --- | --- | --- | --- | --- | --- |
| 9 | − | − | − | − | − | − | − | − |
| 16 | − | − | − | − | − | − | + | − |
| 24 | − | − | − | − | − | − | + | − |
| 46 | − | − | − | − | − | − | + | − |

+ = precipitate observed
++ = heavy precipitate observed

TABLE 3

Samples at 75 mg/mL PMPA, pH 6.5, 60° C. Storage

| Time (days) | 50 ppm $Fe^{3+}$ no EDTA | 50 ppm $Fe^{3+}$ + EDTA | 100 ppm $Fe^{3+}$ no EDTA | 100 ppm $Fe^{3+}$ + EDTA | 50 ppm $Zn^{2+}$ no EDTA | 50 ppm $Zn^{2+}$ + EDTA | 100 ppm $Zn^{2+}$ no EDTA | 100 ppm $Zn^{2+}$ + EDTA |
| --- | --- | --- | --- | --- | --- | --- | --- | --- |
| 9  | − | − | + | − | ++ | − | ++ | − |
| 16 | − | − | − | − | ++ | − | ++ | − |
| 24 | − | − | − | − | +  | − | ++ | − |
| 46 | − | − | − | − | +  | − | ++ | − |

+ = precipitate observed
++ = heavy precipitate observed

TABLE 4

Samples below prepared at 75 mg/mL PMPA, pH 7.5, 60° C. Storage

| Time (days) | 50 ppm $Fe^{3+}$ no EDTA | 50 ppm $Fe^{3+}$ + EDTA | 100 ppm $Fe^{3+}$ no EDTA | 100 ppm $Fe^{3+}$ + EDTA | 50 ppm $Zn^{2+}$ no EDTA | 50 ppm $Zn^{2+}$ + EDTA | 100 ppm $Zn^{2+}$ no EDTA | 100 ppm $Zn^{2+}$ + EDTA |
| --- | --- | --- | --- | --- | --- | --- | --- | --- |
| 9  | − | − | + | − | + | − | ++ | − |
| 16 | − | − | − | − | + | − | +  | − |
| 24 | − | − | − | − | + | − | ++ | − |
| 46 | − | − | − | − | + | − | ++ | − |

+ = precipitate observed
++ = heavy precipitate observed

TABLE 5

Effect of [EDTA] on precipitation in the presence of PMPA (75 mg/mL, pH 6.5), 100 ppm $Zn^{2+}$ stored at 4° C.

| Time (days) | 100 ppm $Zn^{2+}$ 0.01% EDTA | 100 ppm $Zn^{2+}$ 0.005% EDTA | 100 ppm $Zn^{2+}$ 0.0025% EDTA | 100 ppm $Zn^{2+}$ 0.00125% EDTA | 100 ppm $Zn^{2+}$ no EDTA |
| --- | --- | --- | --- | --- | --- |
| 0.62 | n/a | −   | −   | −   | n/a |
| 5    | n/a | +/− | +/− | +/− | n/a |
| 9    | −   | n/a | n/a | n/a | ++  |
| 16   | −   | n/a | n/a | n/a | ++  |
| 24   | −   | n/a | n/a | n/a | +   |
| 27   | n/a | +/− | +   | +   | n/a |
| 46   | −   | n/a | n/a | n/a | ++  |

+/− = haze
+ = precipitate observed
++ = heavy precipitate observed
n/a = precipitate not observed at this time point

TABLE 6

Effect of [EDTA] on precipitation in the presence of PMPA (75 mg/mL, pH 6.5), 100 ppm $Zn^{2+}$ stored at 60° C.

| Time (days) | 100 ppm $Zn^{2+}$ 0.01% EDTA | 100 ppm $Zn^{2+}$ 0.005% EDTA | 100 ppm $Zn^{2+}$ 0.0025% EDTA | 100 ppm $Zn^{2+}$ 0.00125% EDTA | 100 ppm $Zn^{2+}$ no EDTA |
| --- | --- | --- | --- | --- | --- |
| 0.62 | n/a | —   | +   | ++  | n/a |
| 5    | n/a | +/− | +   | ++  | n/a |
| 9    | —   | n/a | n/a | n/a | ++  |
| 16   | —   | n/a | n/a | n/a | ++  |
| 24   | —   | n/a | n/a | n/a | ++  |
| 27   | n/a | +/− | +   | +   | n/a |
| 46   | —   | n/a | n/a | n/a | ++  |

+/− = haze
+ = precipitate observed
++ = heavy precipitate observed
n/a = precipitate not observed at this time point

I claim:

1. A composition comprising a PNA and a sequestering agent.

2. The composition of claim 1 wherein the sequestering agent is a water soluble sequestering agent.

3. The composition of claim 2 wherein the aqueous solution is at a pH of about 6.0–7.5 and contains about 25 mg/mL of the PNA 9-[2-(phosphonomethoxy)propyl] adenine, the water soluble sequestering agent is about 0.1 mg/mL of disodium EDTA and about 10–60 ppm of divalent or trivalent metal cation is present.

4. The composition of claim 2 wherein the aqueous solution is at a pH of about 6.0–7.5 and contains about 25–100 mg/mL of the PNA, the water soluble sequestering agent is about 0.1 mg/mL of disodium EDTA or about 25 mg/mL of citric acid and about 10–60 ppm of divalent or trivalent metal cation is present.

5. The composition of claim 2 wherein the aqueous solution at a pH of about 7.0–7.5 and contains about 75 mg/mL of 9-[2-(phosphonomethoxy)ethyl] adenine, the water soluble sequestering agent is about 0.1 mg/mL of disodium EDTA and about 10–60 ppm of divalent or trivalent metal cation is present.

6. The composition of claim 2 comprising a PNA and a sufficient amount of the water soluble sequestering agent to prevent the appearance of visually detectable precipitate in the composition upon storage of an aqueous solution of the composition containing 5–250 mg/mL of the PNA for at least 6 months at 22°.

7. The composition of claim 6 wherein the sequestering agent is a chelating agent.

8. The composition of claim 7 wherein the chelating agent is EDTA, citric acid or fumaric acid.

9. The composition of claim 8 wherein the composition is an aqueous solution.

10. The composition of claim 9 wherein the aqueous solution contains about 0.001–0.6% w/v of the chelating agent.

11. The composition of claim 10 wherein the divalent or trivalent metal cation is at a concentration of about 2–250 ppm.

12. The composition of claim 11 wherein the divalent or trivalent metal ion is $Fe^{3+}$ or $Zn^{2+}$.

13. The composition of claim 12 wherein the aqueous solution has a pH of about 3.5–9.0.

14. The composition of claim 13 wherein the PNA is an adenyl-containing PNA.

15. The composition of claim 14 wherein the nucleotide analog is 9-[2-(phosphonomethoxy)ethyl] adenine or 9-[2-(phosphonomethoxy)propyl] adenine.

16. The composition of claim 6 wherein the composition comprises a sufficiently low concentration divalent or trivalent metal cation to prevent the appearance of visually detectable precipitate in the composition upon storage of an aqueous solution of the composition containing 5–250 mg/mL of the PNA for at least 6 months at 22°.

17. The composition of claim 8 wherein the composition is an aqueous solution.

18. The composition of claim 17 wherein the aqueous solution has a pH of about 7.0–9.0.

19. The composition of claim 18 wherein the aqueous solution contains about 2–20 ppm of a divalent or trivalent metal cation.

20. The composition of claim 19 wherein the divalent or trivalent metal cation is $Fe^{3+}$ or $Zn^{2+}$.

21. The composition of claim 20 wherein the PNA is an adenyl-containing PNA.

22. The composition of claim 21 wherein the nucleotide analog is 9-[2-(phosphonomethoxy)ethyl] adenine or 9-[2-(phosphonomethoxy)propyl] adenine.

23. The composition of claim 19 wherein the composition comprises a sequestering agent.

24. The composition of claim 23 wherein the sequestering agent is a chelating agent.

25. The composition of claim 24 wherein the chelating agent is EDTA, citric acid or fumaric acid.

26. The composition of claim 25 wherein the aqueous solution contains about 0.001–0.6% w/v of the chelating agent.

27. The composition of claim 6 wherein the composition is an aqueous solution.

28. The composition of claim 27 wherein the aqueous solution has a pH of about 7.0–9.0.

29. The composition of claim 28 wherein the aqueous solution contains about 2–20 ppm of a divalent or trivalent metal cation.

30. The composition of claim 29 wherein the divalent or trivalent metal cation is $Fe^{3+}$ or $Zn^{2+}$.

31. The composition of claim 30 wherein the PNA is an adenyl-containing PNA.

32. The composition of claim 31 wherein the nucleotide analog is 9-[2-(phosphonomethoxy)ethyl] adenine or 9-[2-(phosphonomethoxy)propyl] adenine.

33. The composition of claim 30 wherein the composition comprises a sequestering agent.

34. The composition of claim 33 wherein the sequestering agent is a chelating agent.

35. The composition of claim 34 wherein the chelating agent is EDTA, citric acid or fumaric acid.

36. The composition of claim 34 wherein the aqueous solution contains about 0.001–0.2% w/v of the chelating agent.

37. The composition of claim 36 wherein the PNA is an adenyl-containing PNA.

38. The composition of claim 37 wherein the nucleotide analog is 9-[2-(phosphonomethoxy)ethyl] adenine or 9-[2-(phosphonomethoxy)propyl] adenine.

39. The composition of claim 1 wherein the PNA is an adenyl-containing PNA.

40. The composition of claim 39 wherein the PNA is 9-[2-(phosphonomethoxy)ethyl] adenine or 9-[2-(phosphonomethoxy)propyl] adenine.

41. The composition of claim 40 wherein the composition is an aqueous solution.

42. The composition of claim 41 wherein the sequestering agent is a chelating agent.

43. The composition of claim 42 wherein the chelating agent is EDTA, citric acid or fumaric acid.

44. The composition of claim 43 wherein the aqueous solution contains about 0.001–0.6% w/v of the chelating agent.

45. The composition of claim 44 wherein the divalent or trivalent metal cation is at a concentration of about 2–250 ppm.

46. The composition of claim 45 wherein the divalent or trivalent metal ion is $Fe^{3+}$ or $Zn^{2+}$.

47. The composition of claim 46 wherein the aqueous solution has a pH of about 3.5–9.0.

48. A product produced by the process of mixing a PNA with a sufficient amount of a sequestering agent to prevent the appearance of visually detectable precipitate in the composition upon storage of an aqueous solution of the composition containing 5–250 mg/mL of the PNA for at least 6 months at 22°.

49. The product of claim 48 wherein the sequestering agent is a water soluble sequestering agent.

50. The product of claim 48 wherein the PNA is an adenyl-containing PNA.

51. The product of claim wherein the PNA is 9-[2-(phosphonomethoxy)ethyl] adenine or 9-[2-(phosphonomethoxy)propyl] adenine.

52. The product of claim 44 wherein the product is an aqueous solution.

53. The product of claim 52 wherein the sequestering agent is a chelating agent.

54. The product of claim 53 wherein the chelating agent is EDTA, citric acid or fumaric acid.

55. The product of claim 54 wherein the aqueous solution contains about 0.001–0.6% w/v of the chelating agent.

56. The product of claim 55 wherein the divalent or trivalent metal cation is at a concentration of about 2–250 ppm.

57. The product of claim 56 wherein the divalent or trivalent metal ion is $Fe^{3+}$ or $Zn^{2+}$.

58. The product of claim 57 wherein the aqueous solution has a pH of about 4.0–9.0.

59. A method comprising storing for a period in excess of about 4 months a composition comprising a PNA and (a) a sufficient amount of a sequestering agent, and/or (b) a sufficiently low concentration of a divalent or trivalent metal cation, and/or (c) a sufficient pH in water, to prevent the appearance of visually detectable precipitate in the composition upon storage of an aqueous solution of the composition containing 5–250 mg/mL of the PNA for at least 6 months at 22°.

60. The method of claim 59 wherein the composition is stored at a temperature of greater than 22°.

61. The method of claim 59 wherein the composition is stored at room temperature.

62. The method of claim 59 wherein the composition is stored in a hermetically sealed unit dosage form container.

63. The composition of claim 59 wherein the PNA is an adenyl-containing PNA.

64. The composition of claim 63 wherein the PNA is 9-[2-(phosphonomethoxy)ethyl] adenine or 9-[2-(phosphonomethoxy)propyl] adenine.

65. The composition of claim 64 wherein the composition is an aqueous solution.

66. The composition of claim 65 wherein the sequestering agent is a chelating agent.

67. The composition of claim 66 wherein the chelating agent is EDTA, citric acid or fumaric acid.

68. The composition of claim 67 wherein the aqueous solution contains about 0.001–0.6% w/v of the chelating agent.

69. The method of claim 59 wherein the sequestering agent is a water soluble sequestering agent.

70. The composition of claim 68 wherein the divalent or trivalent metal cation is at a concentration of about 2–250 ppm.

71. The composition of claim 70 wherein the divalent or trivalent metal ion is $Fe^{3+}$ or $Zn^{2+}$.

* * * * *